US012678328B2

(12) United States Patent
Argento et al.

(10) Patent No.: US 12,678,328 B2
(45) **Date of Patent: *Jul. 14, 2026**

(54) INTRAOCULAR SHUNTS WITH LOW-PROFILE ACTUATION ELEMENTS AND ASSOCIATED SYSTEMS AND METHODS

(71) Applicant: Shifamed Holdings, LLC, Campbell, CA (US)

(72) Inventors: Claudio Argento, Felton, CA (US); Richard Lilly, San Jose, CA (US); Robert Chang, Belmont, CA (US); Katherine Sapozhnikov, Campbell, CA (US); Tom Saul, Portland, OR (US)

(73) Assignee: Shifamed Holdings, LLC, Campbell, CA (US)

( * ) Notice: Subject to any disclaimer, the term of this patent is extended or adjusted under 35 U.S.C. 154(b) by 608 days.

This patent is subject to a terminal disclaimer.

(21) Appl. No.: 18/185,249

(22) Filed: Mar. 16, 2023

(65) Prior Publication Data

US 2023/0381021 A1      Nov. 30, 2023

Related U.S. Application Data

(63) Continuation of application No. 17/802,254, filed as application No. PCT/US2021/023238 on Mar. 19, 2021, now Pat. No. 11,766,355.

(Continued)

(51) Int. Cl.
*A61F 9/007*          (2006.01)
*A61F 9/00*            (2006.01)
(52) U.S. Cl.
CPC ........ *A61F 9/00781* (2013.01); *A61F 9/0017* (2013.01)

(58) Field of Classification Search
CPC .......... A61F 9/00781; A61F 2210/0014; A61F 2240/001; A61F 2250/0003; A61F 2250/0013
See application file for complete search history.

(56) References Cited

U.S. PATENT DOCUMENTS

| | | | |
|---|---|---|---|
| 4,401,107 A | 8/1983 | Harber et al. | |
| 4,402,681 A | 9/1983 | Haas et al. | |

(Continued)

FOREIGN PATENT DOCUMENTS

| | | |
|---|---|---|
| AU | 2014201621 B2 | 3/2016 |
| AU | 2016201445 B2 | 3/2016 |

(Continued)

OTHER PUBLICATIONS

International Search Report and Written Opinion received for PCT Application No. PCT/US23/80290, filed on Nov. 17, 2023, Applicant: Shifamed Holdings, LLC, Date of Mailing: May 15, 2024, 12 pages.

(Continued)

*Primary Examiner* — Leslie R Deak
(74) *Attorney, Agent, or Firm* — Perkins Coie LLP

(57) ABSTRACT

The present technology relates to adjustable shunting systems and methods. In some embodiments, the present technology includes an adjustable shunting system that includes a drainage element having an inflow portion configured for placement within a patient. The system can also include a flow control assembly having a gating element operably coupled to the outflow portion of the drainage element. The flow control assembly can further include a first actuation element and a second actuation element coupled to the gating element. The first and second actuation elements can be configured to selectively move the gating element relative to the outflow portion to control an amount of fluid flow therethrough. The first and second actuation elements can (Continued)

each extend less than entirely around a perimeter of the drainage element.

22 Claims, 4 Drawing Sheets

Related U.S. Application Data

(60) Provisional application No. 62/991,701, filed on Mar. 19, 2020.

(56) References Cited

U.S. PATENT DOCUMENTS

| | | | |
|---|---|---|---|
| 4,595,390 | A | 6/1986 | Hakim et al. |
| 5,070,697 | A | 12/1991 | Van Zeggeren |
| 5,123,906 | A | 6/1992 | Kelman |
| 5,476,445 | A | 12/1995 | Baerveldt et al. |
| 5,601,094 | A | 2/1997 | Reiss |
| 5,792,118 | A | 8/1998 | Kurth et al. |
| 6,007,511 | A | 12/1999 | Prywes |
| 6,077,298 | A | 6/2000 | Tu et al. |
| 6,077,299 | A | 6/2000 | Adelberg et al. |
| 6,203,513 | B1 | 3/2001 | Yaron et al. |
| 6,261,256 | B1 | 7/2001 | Ahmed |
| 6,450,984 | B1 | 9/2002 | Lynch et al. |
| 6,508,779 | B1 | 1/2003 | Suson |
| 6,589,203 | B1 | 7/2003 | Mitrev |
| 6,626,858 | B2 | 9/2003 | Lynch et al. |
| 6,638,239 | B1 | 10/2003 | Bergheim et al. |
| 6,666,841 | B2 | 12/2003 | Gharib et al. |
| 6,736,791 | B1 | 5/2004 | Tu et al. |
| 6,789,447 | B1 | 9/2004 | Zinck |
| 7,025,740 | B2 | 4/2006 | Ahmed |
| 7,207,965 | B2 | 4/2007 | Simon |
| 7,354,416 | B2 | 4/2008 | Quiroz-Mereado et al. |
| 7,364,564 | B2 | 4/2008 | Sniegowski et al. |
| 7,458,953 | B2 | 12/2008 | Peyman |
| 7,699,882 | B2 | 4/2010 | Stamper et al. |
| 7,717,872 | B2 | 5/2010 | Shetty |
| 7,947,008 | B2 | 5/2011 | Grahn et al. |
| 8,012,134 | B2 | 9/2011 | Claude et al. |
| 8,157,759 | B2 | 4/2012 | Castillejos |
| 8,206,333 | B2 | 6/2012 | Schmidt et al. |
| 8,206,440 | B2 | 6/2012 | Guarnieri |
| 8,298,240 | B2 | 10/2012 | Giger et al. |
| 8,308,701 | B2 | 11/2012 | Horvath et al. |
| 8,414,635 | B2 | 4/2013 | Hyodoh et al. |
| 8,506,515 | B2 | 8/2013 | Burns et al. |
| 8,540,659 | B2 | 9/2013 | Berlin |
| 8,579,848 | B2 | 11/2013 | Field et al. |
| 8,585,629 | B2 | 11/2013 | Grabner et al. |
| 8,663,303 | B2 | 3/2014 | Horvath et al. |
| 8,702,639 | B2 | 4/2014 | Van Der Mooren et al. |
| 8,721,702 | B2 | 5/2014 | Romoda et al. |
| 8,753,305 | B2 | 6/2014 | Field et al. |
| 8,758,290 | B2 | 6/2014 | Horvath et al. |
| 8,765,210 | B2 | 7/2014 | Romoda et al. |
| 8,771,220 | B2 | 7/2014 | Nissan et al. |
| 8,801,766 | B2 | 8/2014 | Reitsamer et al. |
| 8,828,070 | B2 | 9/2014 | Romoda et al. |
| 8,852,136 | B2 | 10/2014 | Horvath et al. |
| 8,852,137 | B2 | 10/2014 | Horvath et al. |
| 8,852,256 | B2 | 10/2014 | Horvath et al. |
| 8,882,781 | B2 | 11/2014 | Smedley et al. |
| 8,915,877 | B2 | 12/2014 | Cunningham et al. |
| 8,932,247 | B2 | 1/2015 | Stergiopulos |
| 8,974,511 | B2 | 3/2015 | Horvath et al. |
| 9,017,276 | B2 | 4/2015 | Horvath et al. |
| 9,095,411 | B2 | 8/2015 | Horvath et al. |
| 9,095,413 | B2 | 8/2015 | Romoda et al. |
| 9,113,994 | B2 | 8/2015 | Horvath et al. |
| 9,125,723 | B2 | 9/2015 | Horvath et al. |
| 9,192,516 | B2 | 11/2015 | Horvath et al. |
| 9,226,851 | B2 | 1/2016 | Gunn |
| 9,271,869 | B2 | 3/2016 | Horvath et al. |
| 9,283,115 | B2 | 3/2016 | Lind et al. |
| 9,283,116 | B2 | 3/2016 | Romoda et al. |
| 9,289,324 | B2 | 3/2016 | Johnson et al. |
| 9,326,891 | B2 | 5/2016 | Horvath et al. |
| 9,375,347 | B2 | 6/2016 | Stergiopulos |
| 9,393,153 | B2 | 7/2016 | Horvath et al. |
| 9,555,410 | B2 | 1/2017 | Brammer et al. |
| 9,585,789 | B2 | 3/2017 | Silvestrini et al. |
| 9,585,790 | B2 | 3/2017 | Horvath et al. |
| 9,592,154 | B2 | 3/2017 | Romoda et al. |
| 9,610,195 | B2 | 4/2017 | Horvath |
| 9,636,254 | B2 | 5/2017 | Yu et al. |
| 9,636,255 | B2 | 5/2017 | Haffner et al. |
| 9,655,778 | B2 | 5/2017 | Tyler |
| 9,655,779 | B2 | 5/2017 | Bigler et al. |
| 9,693,900 | B2 | 7/2017 | Gallardo Inzunza |
| 9,693,901 | B2 | 7/2017 | Horvath et al. |
| 9,757,276 | B2 | 9/2017 | Penhasi |
| 9,808,373 | B2 | 11/2017 | Horvath et al. |
| 9,877,866 | B2 | 1/2018 | Horvath et al. |
| 9,883,969 | B2 | 2/2018 | Horvath et al. |
| 9,980,854 | B2 | 5/2018 | Horvath et al. |
| 10,004,638 | B2 | 6/2018 | Romoda et al. |
| 10,080,682 | B2 | 9/2018 | Horvath et al. |
| 10,085,884 | B2 | 10/2018 | Reitsamer et al. |
| 10,154,924 | B2 | 12/2018 | Clauson et al. |
| 10,159,600 | B2 | 12/2018 | Horvath et al. |
| 10,195,078 | B2 | 2/2019 | Horvath et al. |
| 10,195,079 | B2 | 2/2019 | Horvath et al. |
| 10,231,871 | B2 | 3/2019 | Hill |
| 10,238,536 | B2 | 3/2019 | Olson et al. |
| 10,285,853 | B2 | 5/2019 | Rangel-Friedman et al. |
| 10,307,293 | B2 | 6/2019 | Horvath et al. |
| 10,314,743 | B2 | 6/2019 | Romoda et al. |
| 10,322,267 | B2 | 6/2019 | Hakim |
| 10,335,030 | B2 | 7/2019 | Alhourani |
| 10,342,703 | B2 | 7/2019 | Siewert et al. |
| 10,363,168 | B2 | 7/2019 | Schieber et al. |
| 10,369,048 | B2 | 8/2019 | Horvath et al. |
| 10,405,903 | B1 | 9/2019 | Biesinger et al. |
| 10,463,537 | B2 | 11/2019 | Horvath et al. |
| 10,470,927 | B2 | 11/2019 | Horvath et al. |
| 10,492,948 | B2 | 12/2019 | Baerveldt |
| 10,524,958 | B2 | 1/2020 | Camras et al. |
| 10,524,959 | B2 | 1/2020 | Horvath |
| 10,596,035 | B2 | 3/2020 | Stergiopulos et al. |
| 10,716,663 | B2 | 7/2020 | Salahieh et al. |
| 10,758,412 | B2 | 9/2020 | Velasquez |
| 10,912,675 | B2 | 2/2021 | Lubatschowski |
| 10,952,897 | B1 | 3/2021 | Smith |
| 10,960,074 | B2 | 3/2021 | Berdahl |
| 11,007,061 | B2 | 5/2021 | Passman et al. |
| 11,039,954 | B2 | 6/2021 | Cohen et al. |
| 11,058,581 | B2 | 7/2021 | Mixter et al. |
| 11,065,154 | B1 | 7/2021 | Sponsel et al. |
| 11,083,624 | B2 | 8/2021 | Stein et al. |
| 11,122,975 | B2 | 9/2021 | Rodger et al. |
| 11,166,847 | B2 | 11/2021 | Badawi et al. |
| 11,166,848 | B2 | 11/2021 | Mixter et al. |
| 11,166,849 | B2 | 11/2021 | Mixter et al. |
| 11,291,585 | B2 | 4/2022 | Schultz et al. |
| 11,517,477 | B2 | 12/2022 | Lilly et al. |
| 11,529,258 | B2 | 12/2022 | Chang et al. |
| 11,737,920 | B2 | 8/2023 | Chang et al. |
| 11,766,355 | B2 * | 9/2023 | Argento ............... A61F 9/0017 |
| | | | 604/8 |
| 11,865,283 | B2 | 1/2024 | Schultz et al. |
| 2001/0011585 | A1 | 8/2001 | Cassidy et al. |
| 2002/0177891 | A1 | 11/2002 | Miles et al. |
| 2002/0193725 | A1 | 12/2002 | Odrich |
| 2003/0079329 | A1 | 5/2003 | Yaron et al. |
| 2003/0127090 | A1 | 7/2003 | Gifford et al. |
| 2003/0163079 | A1 | 8/2003 | Burnett |
| 2003/0183008 | A1 | 10/2003 | Bang et al. |
| 2004/0010219 | A1 | 1/2004 | McCusker et al. |
| 2004/0162545 | A1 | 8/2004 | Brown et al. |
| 2004/0190153 | A1 | 9/2004 | Esch |
| 2004/0193095 | A1 | 9/2004 | Shadduck |

(56) References Cited

U.S. PATENT DOCUMENTS

| | | |
|---|---|---|
| 2004/0254520 A1 | 12/2004 | Porteous et al. |
| 2005/0049578 A1 | 3/2005 | Tu et al. |
| 2005/0059956 A1 | 3/2005 | Varner et al. |
| 2005/0182350 A1 | 8/2005 | Nigam |
| 2005/0196424 A1 | 9/2005 | Chappa |
| 2006/0004317 A1 | 1/2006 | Mauge et al. |
| 2006/0069340 A1 | 3/2006 | Simon |
| 2006/0155300 A1 | 7/2006 | Stamper et al. |
| 2006/0212113 A1 | 9/2006 | Shaolian et al. |
| 2006/0276739 A1 | 12/2006 | Brown |
| 2007/0010837 A1 | 1/2007 | Tanaka |
| 2007/0078371 A1 | 4/2007 | Brown et al. |
| 2007/0088432 A1 | 4/2007 | Solovay et al. |
| 2007/0239161 A1 | 10/2007 | Giger et al. |
| 2007/0265646 A1 | 11/2007 | McCoy et al. |
| 2007/0299487 A1 | 12/2007 | Shadduck |
| 2008/0077071 A1 | 3/2008 | Yaron et al. |
| 2008/0103440 A1 | 5/2008 | Ferren et al. |
| 2008/0119891 A1 | 5/2008 | Miles et al. |
| 2008/0125691 A1 | 5/2008 | Yaron et al. |
| 2008/0277332 A1 | 11/2008 | Liu |
| 2009/0012483 A1 | 1/2009 | Blott et al. |
| 2009/0036818 A1 | 2/2009 | Grahn et al. |
| 2009/0043321 A1 | 2/2009 | Conston et al. |
| 2009/0243956 A1 | 10/2009 | Keilman et al. |
| 2009/0259236 A2 | 10/2009 | Burnett et al. |
| 2009/0287136 A1 | 11/2009 | Castillejos |
| 2009/0314970 A1 | 12/2009 | McAvoy et al. |
| 2009/0326432 A1 | 12/2009 | Schmidt et al. |
| 2009/0326517 A1 | 12/2009 | Bork et al. |
| 2010/0114006 A1 | 5/2010 | Baerveldt |
| 2010/0234791 A1 | 9/2010 | Lynch et al. |
| 2010/0241077 A1 | 9/2010 | Geipel et al. |
| 2010/0249691 A1 | 9/2010 | Van Der Mooren et al. |
| 2010/0331757 A1 | 12/2010 | Claude et al. |
| 2011/0105986 A1 | 5/2011 | Bronstein et al. |
| 2012/0022429 A1 | 1/2012 | Silvestrini et al. |
| 2012/0035525 A1 | 2/2012 | Silvestrini |
| 2012/0065570 A1 | 3/2012 | Yeung et al. |
| 2012/0078220 A1 | 3/2012 | Fallin et al. |
| 2012/0089073 A1 | 4/2012 | Cunningham, Jr. |
| 2012/0232461 A1 | 9/2012 | Seaver et al. |
| 2013/0085440 A1 | 4/2013 | Bohm et al. |
| 2013/0131577 A1 | 5/2013 | Bronstein et al. |
| 2013/0144202 A1 | 6/2013 | Field et al. |
| 2013/0150773 A1 | 6/2013 | Nissan et al. |
| 2013/0150776 A1 | 6/2013 | Bohm et al. |
| 2013/0158381 A1 | 6/2013 | Rickard |
| 2013/0160445 A1 | 6/2013 | Olson et al. |
| 2013/0197621 A1 | 8/2013 | Ryan et al. |
| 2013/0199646 A1 | 8/2013 | Brammer et al. |
| 2013/0205923 A1 | 8/2013 | Brammer et al. |
| 2013/0211312 A1 | 8/2013 | Gelvin |
| 2013/0267887 A1 | 10/2013 | Kahook et al. |
| 2013/0317412 A1 | 11/2013 | Dacquay et al. |
| 2013/0338564 A1 | 12/2013 | Rickard et al. |
| 2014/0046439 A1 | 2/2014 | Dos Santos et al. |
| 2014/0081195 A1 | 3/2014 | Clauson et al. |
| 2014/0213958 A1 | 7/2014 | Clauson et al. |
| 2014/0236066 A1 | 8/2014 | Horvath et al. |
| 2014/0236067 A1 | 8/2014 | Horvath et al. |
| 2014/0236068 A1 | 8/2014 | Van Der Mooren et al. |
| 2014/0309611 A1 | 10/2014 | Wilt et al. |
| 2014/0336560 A1 | 11/2014 | Hakim |
| 2015/0011926 A1 | 1/2015 | Reitsamer et al. |
| 2015/0034217 A1 | 2/2015 | Vad |
| 2015/0045716 A1 | 2/2015 | Gallardo Inzunza |
| 2015/0057592 A1 | 2/2015 | Gunn |
| 2015/0142049 A1 | 5/2015 | Delgado et al. |
| 2015/0230843 A1 | 8/2015 | Palmer et al. |
| 2015/0257931 A1 | 9/2015 | Sanchez et al. |
| 2015/0265469 A1 | 9/2015 | Olson et al. |
| 2015/0313603 A1 | 11/2015 | Bodewadt et al. |
| 2016/0058615 A1 | 3/2016 | Camras et al. |
| 2016/0058616 A1 | 3/2016 | Camras et al. |
| 2016/0067093 A1 | 3/2016 | Johnson et al. |
| 2016/0151179 A1 | 6/2016 | Favier et al. |
| 2016/0220794 A1 | 8/2016 | Negre |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0287439 A1 | 10/2016 | Stergiopulos |
| 2016/0296371 A1 | 10/2016 | Gelvin |
| 2016/0354244 A1 | 12/2016 | Horvath et al. |
| 2016/0354245 A1 | 12/2016 | Horvath et al. |
| 2017/0027582 A1 | 2/2017 | Khoury et al. |
| 2017/0071791 A1 | 3/2017 | Piven |
| 2017/0087016 A1 | 3/2017 | Camras |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0246034 A1 | 8/2017 | Hill |
| 2017/0312125 A1 | 11/2017 | Clauson et al. |
| 2017/0348149 A1 | 12/2017 | Stergiopulos et al. |
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0028366 A1 | 2/2018 | Tout et al. |
| 2018/0092775 A1 | 4/2018 | de Juan, Jr. et al. |
| 2018/0147089 A1 | 5/2018 | Horvath et al. |
| 2018/0177633 A1 | 6/2018 | Haffner et al. |
| 2018/0206878 A1 | 7/2018 | Uspenski et al. |
| 2018/0250166 A1 | 9/2018 | Lubatschowski |
| 2018/0333296 A1 | 11/2018 | Heitzmann et al. |
| 2019/0000673 A1 | 1/2019 | Fjleld et al. |
| 2019/0021907 A1 | 1/2019 | Horvath et al. |
| 2019/0038462 A1 | 2/2019 | Vandiest et al. |
| 2019/0038463 A1 | 2/2019 | Kasic |
| 2019/0046356 A1 | 2/2019 | Laroche |
| 2019/0060118 A1 | 2/2019 | Hill |
| 2019/0121278 A1 | 4/2019 | Kawamura et al. |
| 2019/0133826 A1 | 5/2019 | Horvath et al. |
| 2019/0142632 A1 | 5/2019 | Badawi et al. |
| 2019/0151079 A1 | 5/2019 | Zaldivar |
| 2019/0167475 A1 | 6/2019 | Horvath et al. |
| 2019/0240069 A1 | 8/2019 | Horvath et al. |
| 2019/0247231 A1 | 8/2019 | McClunan |
| 2019/0254873 A1 | 8/2019 | Camras et al. |
| 2019/0274881 A1 | 9/2019 | Romoda et al. |
| 2019/0274882 A1 | 9/2019 | Romoda et al. |
| 2019/0307608 A1 | 10/2019 | Lee et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2019/0358086 A1 | 11/2019 | Camras et al. |
| 2019/0374384 A1 | 12/2019 | Xie et al. |
| 2020/0069469 A1 | 3/2020 | Horvath et al. |
| 2020/0085620 A1 | 3/2020 | Euteneuer et al. |
| 2020/0121503 A1 | 4/2020 | Badawi et al. |
| 2020/0121504 A1 | 4/2020 | Stegmann et al. |
| 2020/0129332 A1 | 4/2020 | Van Der Mooren et al. |
| 2020/0170839 A1 | 6/2020 | Borrmann et al. |
| 2020/0179171 A1 | 6/2020 | Grimaldi et al. |
| 2020/0197157 A1 | 6/2020 | Shmukler et al. |
| 2020/0214891 A1 | 7/2020 | Bigler et al. |
| 2020/0229977 A1 | 7/2020 | Mixter et al. |
| 2020/0229980 A1 | 7/2020 | Horvath |
| 2020/0229981 A1 | 7/2020 | Mixter et al. |
| 2020/0229982 A1 | 7/2020 | Mixter et al. |
| 2020/0246188 A1 | 8/2020 | Horvath et al. |
| 2020/0253725 A1 | 8/2020 | Hadba et al. |
| 2020/0261271 A1 | 8/2020 | Horvath et al. |
| 2020/0276050 A1 | 9/2020 | Simons et al. |
| 2020/0306086 A1 | 10/2020 | Da Silva Curiel et al. |
| 2020/0345549 A1 | 11/2020 | Lu et al. |
| 2020/0376239 A1 | 12/2020 | Heilman et al. |
| 2021/0015665 A1 | 1/2021 | Hacker et al. |
| 2021/0030590 A1 | 2/2021 | Blanda et al. |
| 2021/0038158 A1 | 2/2021 | Haffner et al. |
| 2021/0069486 A1 | 3/2021 | Hakim |
| 2021/0106462 A1 | 4/2021 | Sherwood et al. |
| 2021/0128357 A1 | 5/2021 | de Juan, Jr. et al. |
| 2021/0137736 A1 | 5/2021 | Cavuto et al. |

(56)  References Cited

U.S. PATENT DOCUMENTS

| | | |
|---|---|---|
| 2021/0137737 A1 | 5/2021 | Burns et al. |
| 2021/0161713 A1 | 6/2021 | Bouremel et al. |
| 2021/0196516 A1 | 7/2021 | Ianchulev |
| 2021/0205132 A1 | 7/2021 | Horvath et al. |
| 2021/0212858 A1 | 7/2021 | Tran et al. |
| 2021/0251806 A1 | 8/2021 | Schultz et al. |
| 2021/0282922 A1 | 9/2021 | Cohen-Tzemaeh et al. |
| 2021/0298948 A1 | 9/2021 | Haffner et al. |
| 2021/0315806 A1 | 10/2021 | Haffner |
| 2021/0330499 A1 | 10/2021 | Wardle et al. |
| 2022/0087865 A1 | 3/2022 | Argento et al. |
| 2022/0142818 A1 | 5/2022 | Chang et al. |
| 2022/0160545 A1 | 5/2022 | Mixter et al. |
| 2022/0160546 A1 | 5/2022 | Mixter et al. |
| 2022/0168146 A1 | 6/2022 | Badawi et al. |
| 2022/0202613 A1 | 6/2022 | Chang et al. |
| 2022/0203078 A1 | 6/2022 | May |
| 2022/0241565 A1 | 8/2022 | Nae et al. |
| 2022/0265974 A1 | 8/2022 | Saul et al. |
| 2022/0273491 A1 | 9/2022 | Brown |
| 2022/0339035 A1 | 10/2022 | Lilly et al. |
| 2022/0354695 A1 | 11/2022 | Badawi et al. |
| 2022/0387216 A1 | 12/2022 | Schultz et al. |
| 2022/0387217 A1 | 12/2022 | Argento et al. |
| 2023/0086856 A1 | 3/2023 | Chang et al. |
| 2023/0092196 A1 | 3/2023 | Argento et al. |
| 2023/0146222 A1 | 5/2023 | Kancerevycius et al. |
| 2023/0201544 A1 | 6/2023 | Schultz et al. |
| 2023/0233378 A1 | 7/2023 | Chang et al. |
| 2023/0240891 A1 | 8/2023 | Lilly et al. |
| 2023/0285192 A1 | 9/2023 | Chang et al. |
| 2024/0139029 A1 | 5/2024 | Chang et al. |
| 2024/0173169 A1 | 5/2024 | Schultz et al. |
| 2024/0277522 A1 | 8/2024 | Schultz et al. |
| 2024/0277523 A1 | 8/2024 | Schultz et al. |
| 2024/0325697 A1 | 10/2024 | Schultz et al. |
| 2024/0399122 A1 | 12/2024 | Bronez et al. |

FOREIGN PATENT DOCUMENTS

| | | |
|---|---|---|
| AU | 2018200325 A1 | 2/2018 |
| AU | 2017274654 | 12/2018 |
| AU | 2020201818 | 4/2020 |
| AU | 2017439185 | 5/2020 |
| AU | 2018412569 | 10/2020 |
| BR | 112017025859 A2 | 8/2018 |
| BR | 112020008969 | 10/2020 |
| CA | 2987953 A1 | 12/2016 |
| CA | 3067172 | 12/2018 |
| CA | 3080713 | 5/2019 |
| CA | 3093160 | 9/2019 |
| CN | 101360523 A | 2/2009 |
| CN | 101965211 A | 2/2011 |
| CN | 103476371 | 12/2013 |
| CN | 104490515 | 4/2015 |
| CN | 106726124 | 5/2017 |
| CN | 108743016 A | 11/2018 |
| CN | 111405875 | 7/2020 |
| CO | 2020011460 | 11/2020 |
| DE | 10217061 | 3/2003 |
| DE | 102010015447 | 10/2011 |
| DE | 102010015447 A1 | 10/2011 |
| DE | 102017124885 | 4/2019 |
| DE | 102017124885 A1 | 4/2019 |
| DE | 102018112065 A1 | 11/2019 |
| DE | 102019204846 | 10/2020 |
| DE | 102019204846 A1 | 10/2020 |
| EP | 1292256 A1 | 3/2003 |
| EP | 1737531 A2 | 1/2007 |
| EP | 2552369 | 1/2017 |
| EP | 3302381 A1 | 4/2018 |
| EP | 1765234 | 10/2019 |
| EP | 2999430 | 11/2019 |
| EP | 2677981 | 4/2020 |
| EP | 3659495 | 6/2020 |
| EP | 3518846 | 8/2020 |
| EP | 3666236 | 8/2020 |
| EP | 3687374 | 8/2020 |
| EP | 3706653 | 9/2020 |
| EP | 3730104 | 10/2020 |
| EP | 3735947 | 11/2020 |
| EP | 3773377 | 2/2021 |
| EP | 3846747 | 7/2021 |
| EP | 3846748 | 7/2021 |
| EP | 3329884 | 8/2021 |
| EP | 2389138 | 9/2021 |
| EP | 3870120 | 9/2021 |
| EP | 3313335 | 11/2021 |
| ES | 2725550 | 9/2019 |
| GB | 2602434 | 9/2022 |
| HK | 1252748 | 5/2019 |
| HU | E043303 | 8/2019 |
| JP | 2001-523519 | 11/2001 |
| JP | 2013505065 | 2/2013 |
| JP | 5576427 B2 | 8/2014 |
| JP | 2018-501010 | 1/2018 |
| JP | 2018519892 | 7/2018 |
| JP | 2018130580 | 8/2018 |
| JP | 2018529466 | 10/2018 |
| JP | 2019517366 | 6/2019 |
| JP | 2019205934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO1996019249 | 6/1996 |
| WO | WO2004073564 | 9/2004 |
| WO | WO2004081613 | 9/2004 |
| WO | WO2007011302 A1 | 1/2007 |
| WO | WO2007087061 | 8/2007 |
| WO | WO2009111645 | 9/2009 |
| WO | WO2010111528 | 9/2010 |
| WO | WO2011034740 | 3/2011 |
| WO | WO2012040380 | 3/2012 |
| WO | WO2012113450 | 8/2012 |
| WO | WO2014130574 | 8/2014 |
| WO | WO2016100500 | 6/2016 |
| WO | WO2016149425 | 9/2016 |
| WO | WO2016196841 A1 | 12/2016 |
| WO | WO2017058656 | 4/2017 |
| WO | WO2018229766 | 12/2018 |
| WO | WO2019018807 | 1/2019 |
| WO | WO2019094004 A1 | 5/2019 |
| WO | WO2019165053 | 8/2019 |
| WO | WO2019172940 | 9/2019 |
| WO | WO2020049508 | 3/2020 |
| WO | WO2020150663 | 7/2020 |
| WO | WO2020215068 | 10/2020 |
| WO | WO2020223491 | 11/2020 |
| WO | WO2020231993 | 11/2020 |
| WO | WO2020247365 | 12/2020 |
| WO | WO2020261184 | 12/2020 |
| WO | WO2021007294 | 1/2021 |
| WO | WO2021007296 | 1/2021 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |
| WO | WO2021188952 | 9/2021 |
| WO | WO2021204312 | 10/2021 |

(56) References Cited

FOREIGN PATENT DOCUMENTS

| WO | WO2021212007 | 10/2021 |
| WO | WO2021230887 | 11/2021 |
| WO | WO2022159723 | 7/2022 |
| WO | WO2022175681 | 8/2022 |
| WO | WO2022220861 | 10/2022 |
| WO | WO2023004067 | 1/2023 |
| WO | WO2023278452 | 1/2023 |
| WO | WO2023009366 | 2/2023 |
| WO | WO2023063961 | 4/2023 |
| WO | WO2023064491 | 4/2023 |
| WO | WO2023091307 | 5/2023 |
| WO | WO2023107486 | 6/2023 |
| WO | WO2023215461 | 11/2023 |
| WO | WO2024026397 | 2/2024 |
| WO | WO2024030949 | 2/2024 |
| WO | WO2024097723 | 5/2024 |
| WO | WO2024097743 | 5/2024 |
| WO | WO2024220861 | 10/2024 |
| ZA | 201708295 | 5/2020 |

OTHER PUBLICATIONS

English translation of Japanese Office Action received for Application No. 2022-521301, Applicant: Shifamed Holdings, LLC, Date of Mailing: Jun. 3, 2024, 3 pages.
Extended European Search Report received for EP Application No. 23158246.1, Applicant: Shifamed Holdings, LLC, Date of Mailing: Aug. 7, 2023, 7 pages.
International Search Report and Written Opinion received for PCT Application No. PCT/US23/64636, filed on Mar. 17, 2023, Applicant: Shifamed Holdings, LLC, Date of Mailing: Sep. 5, 2023, 9 pages.
International Search Report and Written Opinion received for PCT Application No. PCT/US23/20973, filed on May 4, 2023, Applicant: Shifamed Holdings, LLC, Date of Mailing: Sep. 21, 2023, 15 pages.
Extended European Search Report received for EP Application No. 20874212.2, Applicant: Shifamed Holdings, LLC, Date of Mailing: Oct. 18, 2023, 8 pages.
Extended European Search Report received for EP Application No. 20875070.3, Applicant: Shifamed Holdings, LLC, Date of Mailing: Dec. 19, 2023, 7 pages.
International Search Report and Written Opinion received for PCT Application No. PCT/US23/71501, filed on Aug. 2, 2023, Applicant: Shifamed Holdings, LLC, Date of Mailing: Jan. 18, 2024, 20 pages.
Extended European Search Report received for EP Application No. 21744394.4, Applicant: Shifamed Holdings, LLC, Date of Mailing: Jan. 26, 2024, 7 pages.
Extended European Search Report received for EP Application No. 21787751.3; Applicant: Shifamed Holdings, LLC, Date of Mailing: Mar. 15, 2024, 8 pages.
International Search Report and Written Opinion received for PCT Application No. PCT/US23/71116, filed on Jul. 27, 2023, Applicant: Shifamed Holdings, LLC, Date of Mailing: Mar. 1, 2024, 12 pages.
Extended European Search Report received for EP Application No. 22743262.2; Applicant: Shifamed Holdings, LLC, Date of Mailing: Oct. 28, 2024, 8 pages.
Collins Dictionary, Textured definition and meaning, 2024, Collins Dictionary, https://www.collinsdictionary.com/dictionary/english/textured, Year: 2024, 1 page.
English translation of Chinese Office Action received for CN Application No. 201880060989.1; Applicant: Shifamed Holdings, LLC, Date of Mailing: Oct. 18, 2024, 9 pages.
International Search Report and Written Opinion received for PCT Application No. PCT/US18/43158, filed on Jul. 20, 2018, Applicant: Shifamed Holdings, LLC, Date of Mailing: Nov. 23, 2018, 12 pages.
International Search Report and Written Opinion received for PCT Application No. PCT/US20/14186, filed on Jan. 17, 2020, Applicant: Shifamed Holdings, LLC, Date of Mailing: Jun. 4, 2020, 13 pages.
International Search Report and Written Opinion received for PCT Application No. PCT/US21/14774, filed on Jan. 22, 2021, Applicant: Shifamed Holdings, LLC, Date of Mailing: May 12, 2021, 10 pages.
International Search Report and Written Opinion received for PCT Application No. PCT/US21/17962, filed on Feb. 12, 2021, Applicant: Shifamed Holdings, LLC, Date of Mailing: Jun. 7, 2021, 12 pages.
International Search Report and Written Opinion received for PCT Application No. PCT/US21/23238, filed on Mar. 19, 2021, Applicant: Shifamed Holdings, LLC, Date of Mailing: Jul. 8, 2021, 10 pages.
International Search Report and Written Opinion received for PCT Application No. PCT/US21/18601, filed on Feb. 18, 2021, Applicant: Shifamed Holdings, LLC, Date of Mailing: Jul. 19, 2021, 12 pages.
International Search Report and Written Opinion received for PCT Application No. PCT/US21/27742, filed on Apr. 16, 2021, Applicant: Shifamed Holdings, LLC, Date of Mailing: Oct. 7, 2021, 13 pages.
International Search Report and Written Opinion received for PCT Application No. PCT/US21/49140, filed on Sep. 3, 2021, Applicant: Shifamed Holdings, LLC, Date of Mailing: Dec. 7, 2021, 22 pages.
International Search Report and Written Opinion received for PCT Application No. PCT/US21/55258, filed on Oct. 15, 2021, Applicant: Shifamed Holdings, LLC, Date of Mailing: Feb. 28, 2022, 18 pages.
International Search Report and Written Opinion received for PCT Application No. PCT/US20/55144, filed on Oct. 9, 2020, Applicant: Shifamed Holdings, LLC, Date of Mailing: Feb. 1, 2021, 16 pages.
International Search Report and Written Opinion received for PCT Application No. PCT/US20/55141, filed on Oct. 9, 2020, Applicant: Shifamed Holdings, LLC, Date of Mailing: Jan. 29, 2021, 11 pages.
International Search Report and Written Opinion received for PCT Application No. PCT/US22/13336, filed on Jan. 21, 2022, Applicant: Shifamed Holdings, LLC, Date of Mailing: Apr. 11, 2022, 9 pages.
International Search Report and Written Opinion received for PCT Application No. PCT/US22/37917, filed on Jul. 21, 2022, Applicant: Shifamed Holdings, LLC, Date of Mailing: Dec. 15, 2022, 15 pages.
Keulegan et al. "Pressure Losses for Fluid Flow in Curved Pipes," Journal of Research of the National Bureau of Standards, vol. 18, Jan. 31, 1937 (Jan. 31, 1937), 26 pages.
Olsen et al. "Human sclera: thickness and surface area," American Journal of Ophthalmology, vol. 125, Issue. 2, https://pubmed.ncbi.nlm.nih.gov/9467451, Feb. 1, 1998 (Feb. 1, 1998), 1 page.
International Search Report and Written Opinion received for PCT Application No. PCT/US22/048863, filed on Nov. 3, 2022, Applicant: Shifamed Holdings, LLC, Date of Mailing: Feb. 16, 2023, 13 pages.
International Search Report and Written Opinion received for PCT Application No. PCT/US2021/023238, filed on Mar. 19, 2021, Applicant: Shifamed Holdings, LLC, Date of Mailing: Jul. 8, 2021, 10 pages.
International Search Report and Written Opinion received for PCT Application No. PCT/US22/52002, filed on Dec. 6, 2022, Applicant: Shifamed Holdings, LLC, Date of Mailing: Mar. 21, 2023, 11 pages.
International Search Report and Written Opinion received for PCT Application No. PCT/US22/46604, filed on Oct. 13, 2022, Applicant: Shifamed Holdings, LLC, Date of Mailing: Mar. 30, 2023, 11 pages.
International Search Report and Written Opinion received for PCT Application No. PCT/US24/25489, Applicant: Shifamed Holdings, LLC, Date of Mailing: Sep. 9, 2024, 18 pages.

* cited by examiner

INTRAOCULAR SHUNTS WITH LOW-PROFILE ACTUATION ELEMENTS AND ASSOCIATED SYSTEMS AND METHODS

CROSS-REFERENCE TO RELATED APPLICATION(S)

This is a continuation of U.S. patent application Ser. No. 17/802,254, filed Aug. 25, 2022, which is a 35 U.S.C. § 371 U.S. National Phase application of International Patent Application No. PCT/US2021/023238, filed Mar. 19, 2021, which claims priority to U.S. Provisional Patent Application No. 62/991,701, filed Mar. 19, 2020, each of which is herein incorporated by reference in its entirety.

TECHNICAL FIELD

The present technology generally relates to implantable medical devices and, in particular, to intraocular shunting systems and associated methods for selectively controlling fluid flow between different portions of a patient's eye.

BACKGROUND

Glaucoma is a degenerative ocular condition involving damage to the optic nerve that can cause progressive and irreversible vision loss. Glaucoma is frequently associated with ocular hypertension, an increase in pressure within the eye resultant from an increase in production of aqueous humor ("aqueous") within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the capillary bed in the sclera of the eye. Glaucoma is typically caused by a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1A:
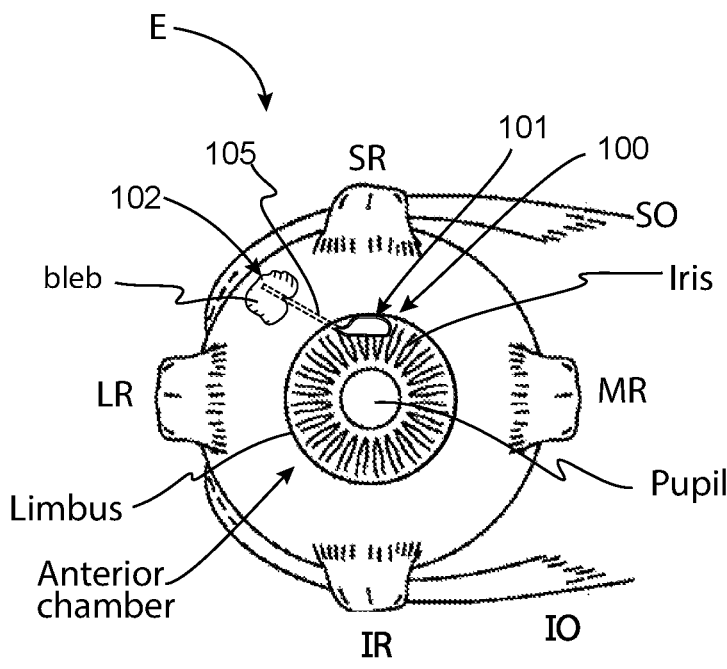
FIG. 1A is a simplified front view of an eye with an implanted shunt configured in accordance with an embodiment of the present technology.

The present technology is generally directed to adjustable intraocular shunting systems (also referred to herein as "intraocular shunts" or "shunts") for treating glaucoma. An intraocular shunting system configured in accordance with an embodiment of the present technology can include, for example, a drainage element configured to shunt fluid from the anterior chamber of the eye to a different location (e.g., to a subconjunctival bleb space). The drainage element can be coupled to a flow control assembly configured to selectively adjust fluid flow therethrough. In some embodiments, the flow control assembly includes a gating element operably coupled to the drainage element such that the amount of fluid flow varies based on the position of the gating element. The flow control assembly can further include at least one actuation element (e.g., first and second actuation elements) coupled to the gating element to control the positioning thereof. The actuation element(s) can have a low-profile shape that extends only partially around the perimeter of the drainage element. The low-profile shape is expected to improve accessibility of the actuation element(s) for actuation, e.g., by application of energy from an external source. As a result, the intraocular shunting systems of the present technology can be used to non-invasively adjust the amount of fluid flow from the anterior chamber of the eye to selectively modulate the pressure therein.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-3D.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. Reference throughout this specification to the term "resistance" refers to fluid resistance unless the context clearly dictates otherwise. The terms "drainage rate," "flow rate," and "flow" are used interchangeably to describe the movement of fluid through a structure.

Although certain embodiments herein are described in terms of shunting fluid from an anterior chamber of an eye, one of skill in the art will appreciate that the present technology can be readily adapted to shunt fluid from and/or between other portions of the eye. Moreover, while the certain embodiments herein are described in the context of glaucoma treatment, any of the embodiments herein, including those referred to as "glaucoma shunts" or "glaucoma devices" may nevertheless be used and/or modified to treat other diseases or conditions of the eye, including other diseases or conditions of the eye or other body regions. For example, the systems described herein can be used to treat diseases characterized by increased pressure and/or fluid build-up, including but not limited to heart failure (e.g., heart failure with preserved ejection fraction, heart failure with reduced ejection fraction, etc.), pulmonary failure, renal failure, hydrocephalus, and the like. Moreover, while generally described in terms of shunting aqueous, the systems described herein may be applied equally to shunting other fluid, such as blood or cerebrospinal fluid, between the first body region and the second body region (e.g., an interatrial shunt device, etc.).

The headings provided herein are for convenience only and do not interpret the scope or meaning of the claimed present technology.

A. Intraocular Shunts for Glaucoma Treatment

Glaucoma refers to a group of eye diseases associated with damage to the optic nerve which eventually results in vision loss and blindness. As noted above, glaucoma is a degenerative ocular condition often characterized by an increase in pressure within the eye resulting from an increase in production of aqueous within the eye and/or a decrease in the rate of outflow of aqueous from within the eye into the blood stream. The increased pressure leads to injury of the optic nerve over time. Unfortunately, patients often do not present with any symptoms until they start to lose their vision. As such, patients typically must be closely monitored if they are at risk for developing glaucoma even if they are not symptomatic. The monitoring continues throughout an at-risk patient's life so clinicians can intervene early to stem progression of the disease. Monitoring pressure requires patients to visit a clinic site on a regular basis which is expensive, time-consuming, and inconvenient. The early stages of glaucoma are typically treated with drugs (e.g., eye drops) and/or laser therapy. When drug/laser treatments no longer suffice, however, surgical approaches can be used. Surgical or minimally invasive approaches primarily attempt to increase the outflow of aqueous from the anterior chamber to the blood stream either by the creation of alternative fluid paths or the augmentation of the natural paths for aqueous outflow.

Figure 1B:
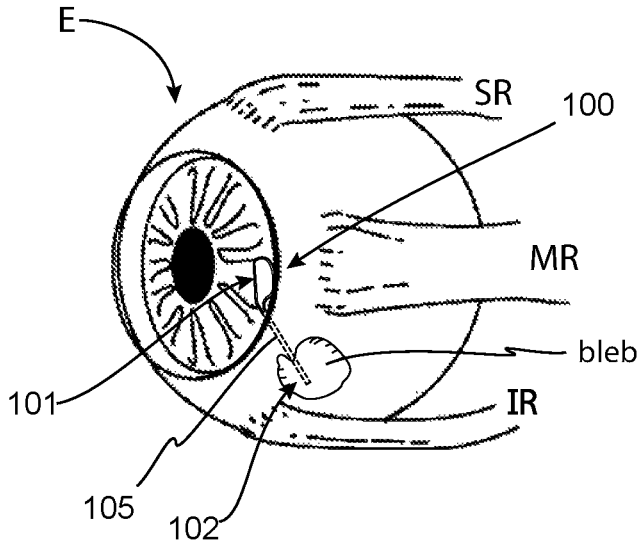
FIG. 1B is an isometric view of the eye and implanted shunt of FIG. 1A.

FIGS. 1A and 1B illustrate a human eye E and suitable location(s) in which a shunt may be implanted within the eye E in accordance with embodiments of the present technology. More specifically, FIG. 1A is a simplified front view of the eye E with an implanted shunt 100, and FIG. 1B is an isometric view of the eye E and the shunt 100 of FIG. 1A. Referring first to FIG. 1A, the eye E includes a number of muscles to control its movement, including a superior rectus SR, inferior rectus IR, lateral rectus LR, medial rectus MR, superior oblique SO, and inferior oblique 10. The eye E also includes an iris, pupil, and limbus.

Referring to FIGS. 1A and 1B together, the shunt 100 can have a drainage element 105 (e.g., a drainage tube) positioned such that an inflow portion 101 is positioned in an anterior chamber of the eye E, and an outflow portion 102 is positioned at a different location within the eye E, such as a bleb space. The shunt 100 can be implanted in a variety of orientations. For example, when implanted, the drainage element 105 may extend in a superior, inferior, medial, and/or lateral direction from the anterior chamber. Depending upon the design of the shunt 100, the outflow portion 102 can be placed in a number of different suitable outflow locations (e.g., between the choroid and the sclera, between the conjunctiva and the sclera, etc.).

Outflow resistance can change over time for a variety of reasons, e.g., as the outflow location goes through its healing process after surgical implantation of a shunt (e.g., shunt 100) or further blockage in the drainage network from the anterior chamber through the trabecular meshwork, Schlemm's canal, the collector channels, and eventually into the vein and the body's circulatory system. Further, in some rare instances, production of aqueous may increase. Accordingly, a clinician may desire to modify the shunt after implantation to either increase or decrease the outflow resistance in response to such changes or for other clinical reasons. For example, in many procedures the shunt is modified at implantation to temporarily increase its outflow resistance. After a period of time deemed sufficient to allow for healing of the tissues and stabilization of the outflow resistance, the modification to the shunt is reversed, thereby decreasing the outflow resistance. In another example, the clinician may implant the shunt and after subsequent monitoring of intraocular pressure determine a modification of the drainage rate through the shunt is desired. Such modifications can be invasive, time-consuming, and/or expensive for patients. If such a procedure is not followed, however, there is a high likelihood of creating hypotony (excessively low eye pressure), which can result in further complications, including damage to the optic nerve. In contrast, intraocular shunting systems configured in accordance with embodiments of the present technology allow the clinician to selectively adjust the flow of fluid through the shunt after implantation without additional invasive surgical procedures.

The shunts described herein can be implanted having a first drainage rate and subsequently remotely adjusted to achieve a second, different drainage rate. The adjustment can be based on the needs of the individual patient. For example, the shunt may be implanted at a first lower flow rate and subsequently adjusted to a second higher flow rate as clinically necessary. The shunts described herein can be delivered using either ab interno or ab externo implant techniques, and can be delivered via needles. The needles can have a variety of shapes and configurations to accommodate the various shapes of the shunts described herein. Details of an implant procedure, implant devices, and bleb formation are described in greater detail in International Patent Application No. PCT/US20/41152, filed Jul. 8, 2020, the disclosure of which is incorporated by reference herein for all purposes.

In many of the embodiments described herein, the flow control assemblies are configured to introduce features that selectively impede or selectively attenuate fluid flow through the shunt during operation. In this way, the flow control assemblies can incrementally or continuously change the flow resistance through the shunt to selectively regulate pressure and/or flow (e.g., maximize flow and/or minimize resistance). The flow control assemblies configured in accordance with the present technology can accordingly adjust the level of interference or compression between a number of different positions, and accommodate a multitude of variables (e.g., IOP, aqueous production rate, native aqueous outflow resistance, and/or native aqueous outflow rate) to precisely regulate flow rate through the shunt.

The disclosed flow control assemblies can be operated using energy. This feature allows such devices to be implanted in the patient and then modified/adjusted over time without further invasive surgeries or procedures for the patient. Further, because the devices disclosed herein may be actuated via energy from an external energy source (e.g., a laser), such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

B. Operation of Actuation Elements

Some embodiments of the present technology include actuation assemblies (e.g., flow control assemblies or flow control mechanisms) that have at least two actuation elements coupled to a moveable element (e.g., a gating element). As described in detail below, the moveable element can be formed to interface with (e.g., at least partially block) a corresponding port. The port can be an inflow port or an outflow port. Movement of the actuation elements generates movement of the moveable element. The movement can be translational and/or rotational.

The actuation element(s) can include a shape memory material (e.g., a shape memory alloy, or a shape memory polymer). Movement of the actuation element(s) can be generated through applied stress and/or use of a shape memory effect (e.g., as driven by a change in temperature). The shape memory effect enables deformations that have altered an element from its preferred geometric configuration (e.g., original or fabricated configuration, shape-set configuration, heat-set configuration, etc.) to be largely or entirely reversed during operation of the flow control assembly. For example, thermal actuation (heating) can reverse deformation(s) by inducing a change in state (e.g., phase change) in the actuator material, inducing a temporary elevated internal stress that promotes a shape change toward the preferred geometric configuration. For a shape memory alloy, the change in state can be from a martensitic phase (alternatively, R-phase) to an austenitic phase. For a shape memory polymer, the change in state can be via a glass transition temperature or a melting temperature. The change in state can reverse deformation(s) of the material—for example, deformation with respect to its preferred geometric configuration—without any (e.g., externally) applied stress to the actuation element. That is, a deformation that is present in the material at a first temperature (e.g., body temperature) can be (e.g., thermally) recovered and/or altered by raising the material to a second (e.g., higher) temperature. Upon cooling (and changing state, e.g., back to martensitic phase), the actuation element retains its preferred geometric configuration. With the material in this relatively cooler-temperature condition it may require a lower force or stress to thermoelastically deform the material, and any subsequently applied external stress can cause the actuation element to once again deform away from the original geometric configuration.

The actuation element(s) can be processed such that a transition temperature at which the change in state occurs (e.g., the austenite start temperature, the austenite final temperature, etc.) is above a threshold temperature (e.g., body temperature). For example, the transition temperature can be set to be about 45 deg. C., about 50 deg. C., about 55 deg. C., or about 60 deg. C. In some embodiments, the actuator material is heated from body temperature to a temperature above the austenite start temperature (or alternatively above the R-phase start temperature) such that an upper plateau stress (e.g., "UPS_body temperature") of the material in a first state (e.g., thermoelastic martensitic phase, or thermoelastic R-phase at body temperature) is lower than an upper plateau stress (e.g., "UPS_actuated temperature") of the material in a heated state (e.g., superelastic state), which achieves partial or full free recovery. For example, the actuator material can be heated such that UPS_actuated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase at body temperature") is lower than a lower plateau stress (e.g., "LPS") of the material in a heated state (e.g., superelastic state), which achieves partial or full free recovery. For example, the actuator material can be aged such that LPS_activated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase) is higher than a lower plateau stress of the material in a heated state, which achieves partial free recovery. For example, the actuator material can be aged such that LPS_activated temperature<UPS_body temperature.

The flow control assembly can be formed such that the actuation elements have substantially the same preferred geometric configuration (e.g., memory shape, or length, L0). The flow control assembly can be assembled such that, upon introduction into a patient (e.g., implantation), at least one (e.g., a first) actuation element/shape memory element has been deformed with respect to its preferred geometric configuration (e.g., to have L1≠L0), while at least one other opposing (e.g., a second) actuation element/shape memory element positioned adjacent to the first actuation element is substantially at its preferred geometric configuration (e.g., L0). In other embodiments, however, both the first and second actuation elements may be deformed with respect to their corresponding preferred geometric configuration upon introduction into the patient (e.g., the first actuation element is contracted relative to its preferred geometric configuration and the second actuation element is expanded relative to its preferred geometric configuration).

In some embodiments of the present technology, L1>L0—for example, the deformed first actuation element is elongated with respect to its preferred "shape memory" length. In some embodiments, L1<L0—for example, the deformed first actuation element is compressed with respect to its preferred shape memory length. The flow control assembly can be formed such that, in operation, its overall dimension (e.g., overall length) is substantially fixed (e.g., L0+L1=a constant). For example, (e.g., outermost) ends of the actuation elements can be fixed, such that movement of the actuation elements occurs between the points of fixation. The overall geometry of the actuation elements, along with the lengths, can be selected such that, in operation, deformation within the actuation elements remains below about 10%, about 9%, about 8%, about 7%, or about 6%.

The (e.g., first and second) actuation elements are arranged such that a movement (e.g., deflection or deformation) of the first actuation element/first shape memory element is accompanied by (e.g., causes) an opposing movement of the second actuation element/second shape memory element. The movement can be a deflection or a deformation. In operation, selective heating of the first actuation element of the flow control assembly causes it to move to and/or toward its preferred geometric configuration (e.g., revert from L1 to L0), moving the coupled moveable element. At the same time, the elongation of the first actuation element is accompanied by (e.g., causes) a compression of the second actuation element (e.g., from L0 to L1). The second actuation element is not heated (e.g., remains at body temperature), and therefore the second actuation element deforms (e.g., remains martensitic and compresses). The first actuation element cools following heating, and returns to a state in which it can be plastically deformed. To reverse the configuration of the flow control assembly (e.g., the position of the moveable element), the second actuation element is heated to move to and/or toward its preferred geometric configuration (e.g., from L1 to L0). The return of the second actuation element to its preferred geometric configuration causes the moveable element to move back to its prior position, and compresses the first actuation element (e.g., from L0 to L1). The position of the moveable element for the flow control assembly can be repeatedly toggled (e.g., between open and closed) by repeating the foregoing operations. The heating of an actuation element can be accomplished via application of incident energy (e.g., via a laser or inductive coupling). Further, as mentioned above, the source of the incident energy may be external to the patient (e.g., non-invasive).

C. Flow Control Assemblies for Intraocular Shunting Systems

As provided above, the present technology is generally directed to intraocular shunting systems. Such systems include a drainage element (e.g., an elongated flow tube) configured to shunt fluid away from the anterior chamber of the eye. For example, the drainage element can include an inflow portion configured for placement within the anterior chamber (e.g., at a location away from the optical field of view) and an outflow portion configured for placement at a different location of the eye (e.g., at a subconjunctival bleb space). To selectively control fluid flow through the drainage element (e.g., post-implantation), the system further includes a flow control assembly operably coupled to the drainage element. In some embodiments, the flow control assembly includes a gating element operably coupled to a portion of the drainage element (e.g., to the outflow portion). The gating element can be movable relative to the portion of the drainage element such that the positioning of the gating element modulates the amount of the fluid flow from the drainage element.

The flow control assembly can also include a first actuation element and a second actuation element coupled to the gating element and configured to control the movement thereof. In some embodiments, the first and second actuation elements each have a low-profile shape (e.g., a flattened or partially flattened shape). For example, rather than wrapping entirely around the entire perimeter of the drainage element, the first and second actuation elements can extend only partially around the drainage element so that the length of the interface region therebetween is less than the perimeter of the drainage element (e.g., as depicted in FIGS. 3A-3D and described in greater detail below). The low-profile shape is expected to improve accessibility of the first and second actuation elements to non-invasive actuation (e.g., by application of energy from a source external to the patient). An increase in accessibility can refer to an increased proportion of the actuator that is accessible to non-invasive actuation. The low-profile shape can reduce a frictional force experienced by the gating element and/or the actuation element(s) during movement. The reduced frictional force can be a reduction with respect to a flow control assembly having a first actuation element and/or a second actuation element that extend fully around the drainage element.

Figure 2A:
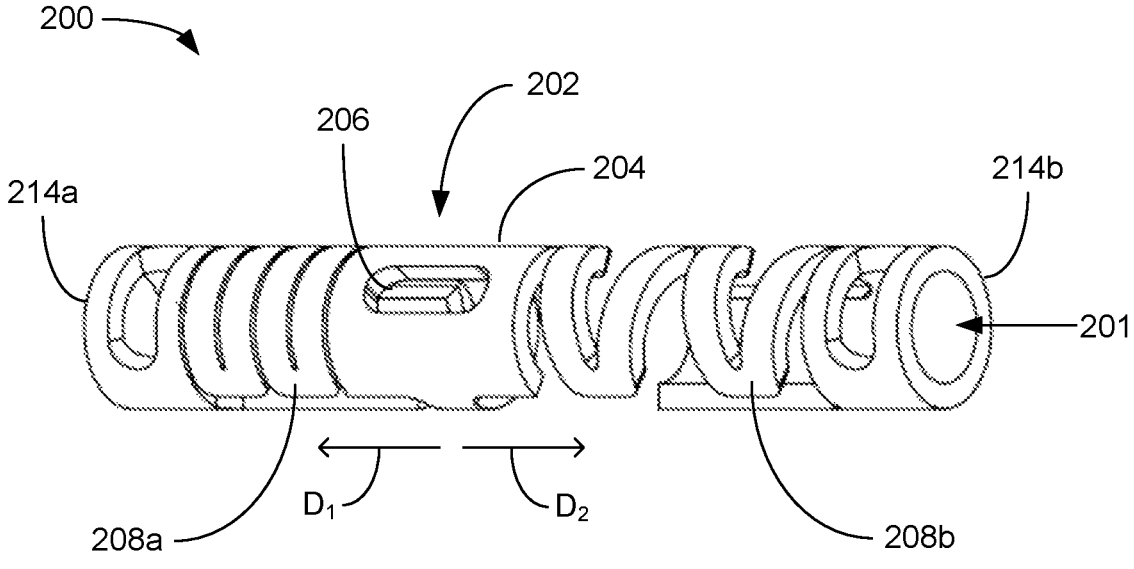
FIGS. 2A-2D illustrate a flow control assembly of an intraocular shunting system configured in accordance with an embodiment of the present technology.
Figure 2B:
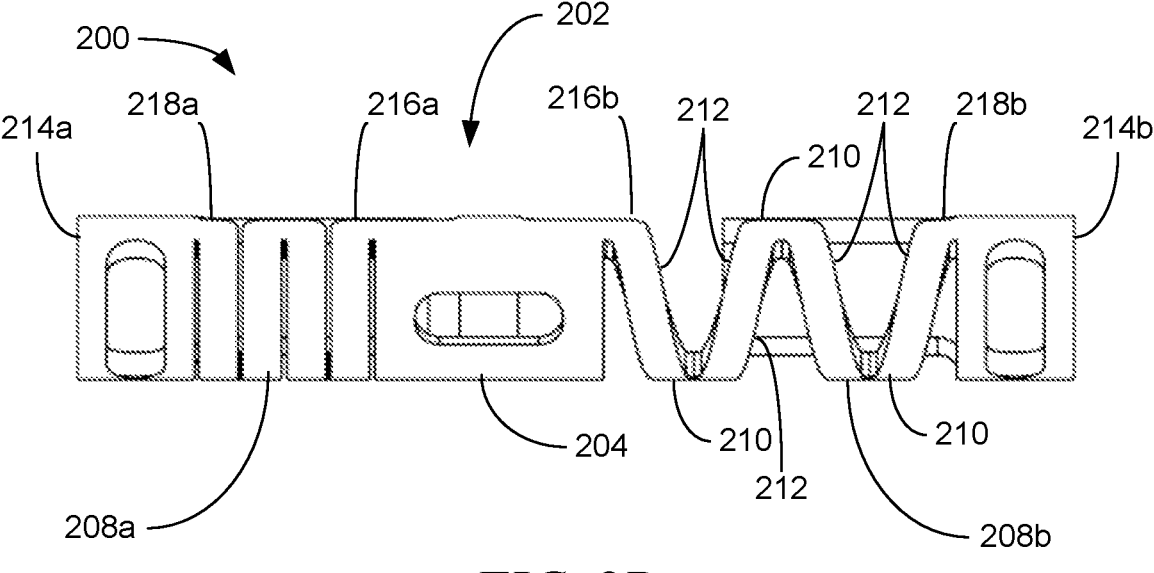
Figure 2C:
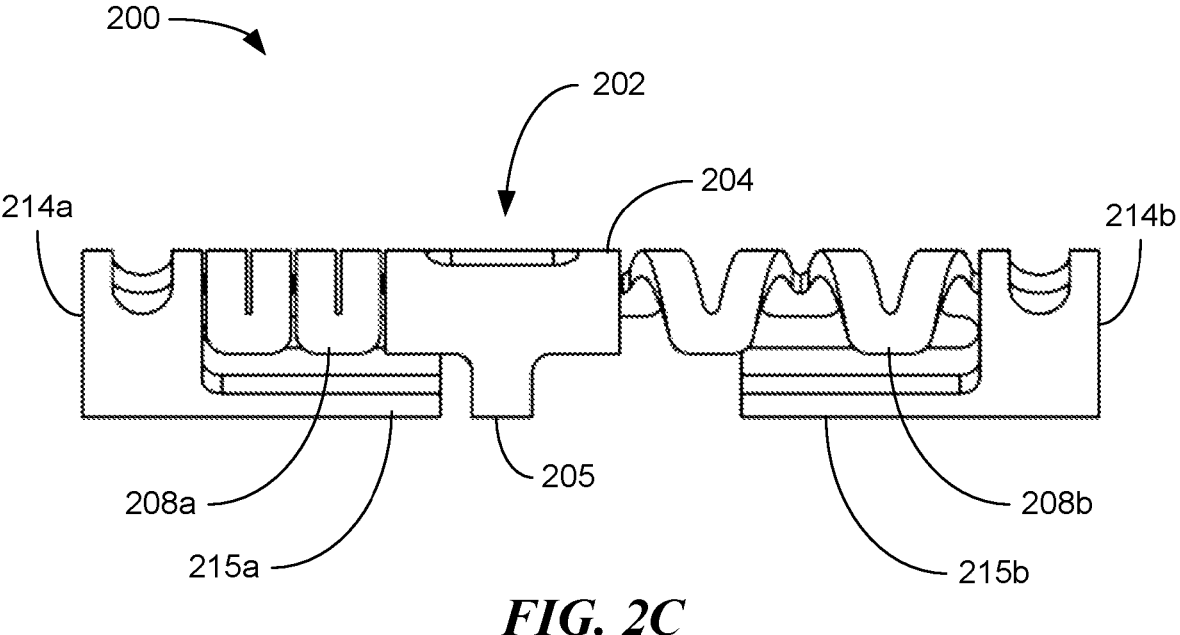
Figure 2D:
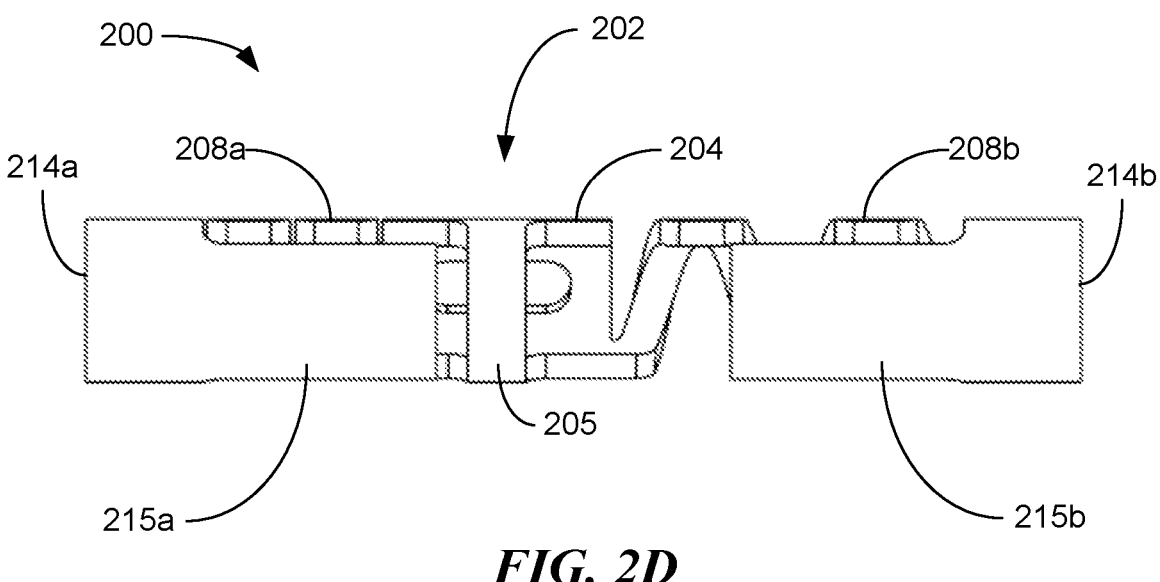

FIGS. 2A-2D, for example, illustrate a flow control assembly 200 of an intraocular shunting system configured in accordance with an embodiment of the present technology. More specifically, FIG. 2A is an isometric view of the flow control assembly 200, and FIGS. 2B-2D are front views of the flow control assembly 200 in different states during operation. The flow control assembly 200 can be operably coupled to an outflow portion of a drainage element (not shown) to selectively control fluid flow therethrough (e.g., to modulate pressure within the anterior chamber of the eye). As described in greater detail below, the fluid resistance of the system, and thus the drainage of aqueous through system, can be precisely controlled by selectively blocking and/or unblocking fluid inlets by actuating corresponding actuation elements of the flow control assembly 200.

As best seen in FIG. 2A, the flow control assembly 200 can be an elongated hollow structure with a lumen 201 extending therethrough. The lumen 201 can be shaped to receive the outflow portion. In some embodiments, the cross-sectional shape of the lumen 201 is identical or generally similar to the cross-sectional shape of the outflow portion. In other embodiments, however, the cross-sectional shape of the lumen 201 can be different from the cross-sectional shape of the outflow portion. Although the illustrated embodiment shows the flow control assembly 200 as being generally tubular or cylindrical with a circular cross-sectional shape, in other embodiments the flow control assembly 200 can have a different cross-sectional shape (e.g., a semicircular, elliptical, semielliptical, square, rectangular, polygonal, curvilinear, rectilinear, or other shape).

Referring to FIGS. 2A-2D together, the flow control assembly 200 includes a gating element 202 operably coupled to the outflow portion such that the amount of fluid flow from the outflow portion varies based on the positioning of the gating element 202 relative to the outflow portion. The gating element 202 can be a shuttle, valve, or any other structure that is movable relative to the outflow portion. For example, the gating element 202 can be configured to move along the longitudinal axis of the outflow portion in a first direction $D_1$ and/or a second, opposite direction $D_2$ (FIG. 2A).

In some embodiments, the outflow portion includes one or more apertures formed therein to permit fluid outflow (e.g., similar to the outflow ports 102 described with respect to FIGS. 1A and 1B). The gating element 202, for example, can be positioned near or adjacent to the aperture(s) such that, depending on the position of the gating element 202, one or more apertures can be obstructed or unobstructed by the gating element 202. For example, the gating element 202 can include a shuttle structure 204 with an opening 206 formed therein. When the gating element 202 is in a first position, the opening 206 can be positioned adjacent, near, over, or otherwise generally aligned with the aperture(s) such that the aperture(s) are accessible. As a result, fluid can flow from the outflow portion with little or no obstruction. When the gating element 202 is in a second position, the opening 206 can be spaced apart, offset, or otherwise located away from the aperture(s) such that the shuttle structure 204 partially or completely covers the aperture(s). As a result, the fluid flow from the outflow portion can be partially or completely obstructed by the gating element 202.

In some embodiments, the gating element 202 is movable between two positions, e.g., an "open" position permitting fluid flow and a "closed" position obstructing fluid flow. In other embodiments the gating element 202 is movable between a plurality of different positions to allow for incremental adjustments to the amount of fluid flow. In such embodiments the amount of fluid flow can vary based on the number of covered aperture(s), the number of accessible aperture(s), the extent to which each aperture is covered by the shuttle structure 204, and/or the extent to which each aperture is aligned with the opening 206.

The gating element 202 can be configured to move primarily or only in a linear direction along the longitudinal axis of the outflow portion (e.g., along $D_1$ and/or $D_2$—FIG. 2A), with little or no movement in other directions (e.g., outwardly away from the longitudinal axis, circumferentially around the longitudinal axis, rotationally, etc.). In some embodiments, the gating element 202 extends around the entire perimeter of the outflow portion to constrain the gating element 202 to linear movements along the longitudinal axis and reduce or inhibit undesired movements (e.g., due to deformation, warping, etc.). For example, as best seen in FIGS. 2C and 2D, the gating element 202 can include a retention structure 205 connected to the shuttle structure 204. In the illustrated embodiment, the retention structure 205 has an elongated, arcuate and/or curved shape (e.g., a semi-annular shape). The shuttle structure 204 can extend around a region of the outflow portion (e.g., a front and/or upper surface—not shown) and the retention structure 205 can extend around the remaining regions of the outflow portion (e.g., a back and/or lower surface—not shown) such that these components collectively extend around the entire perimeter of the outflow portion.

The flow control assembly 200 further includes a first actuation element 208a and a second actuation element 208b configured to selectively control the movement of the gating element 202. The gating element 202 can be positioned between the first and second actuation elements 208a-b such that the first actuation element 208a is coupled to a first side of the gating element 202 (e.g., to shuttle structure 204) and the second actuation element 208b is coupled to a second, opposite side of the gating element 202 (e.g., to shuttle structure 204). The first and second actuation elements 208a-b can be individually and/or collectively actuatable to adjust the positioning of the gating element 202 relative to the outflow portion, as described in greater detail below.

In some embodiments, the first and second actuation elements 208a-b each have a low-profile shape such that the first and second actuation elements 208a-b extend only partially around the outflow portion, rather than completely around the outflow portion (e.g., in contrast to the gating element 202). For example, the first and second actuation elements 208a-b can be adjacent or near a front and/or upper surface of the outflow portion, and can be spaced apart from a back and/or lower surface of the outflow portion. The low-profile shape can be a flattened and/or planar shape. In other embodiments the low-profile shape can be a curved and/or arcuate shape (e.g., as shown in FIGS. 2A-2D).

The geometry of the first and second actuation elements 208a-b can be configured in a number of different ways. For example, as best seen in FIG. 2B, the first and second actuation elements 208a-b can each include a plurality of apices or bend regions 210 and a plurality of struts 212 interconnected with each other to form a serpentine or "zig-zag"-shaped structure (reference numbers are shown only for the apices and struts of the second actuation element 208b merely for purposes of clarity). In some embodiments, the apices 210 and struts 212 of an individual actuation element lie in the same plane so that the actuation element has a flattened and/or planar low-profile shape. In other embodiments, however, the apices 210 and struts 212 of an individual actuation element can lie along a non-planar and/or curved surface (e.g., a cylindrical surface) so that the actuation element has a curved and/or arcuate low-profile shape.

In the illustrated embodiment, the first and second actuation elements 208a-b each have three apices 210 and four struts 212. In other embodiments, however, the first and second actuation elements 208a-b can include a different number of apices (e.g., one, two, four, five, or more) and/or a different number of struts (e.g., one, two, three, five, or more). Additionally, although FIG. 2B illustrates the apices 210 as having a generally flattened shape, in other embodiments the apices 210 can have other shapes (e.g., sharp, angular, curved, rounded, etc.). Likewise, although struts 212 are depicted as being generally linear, in other embodiments the struts 212 can have other geometries (e.g., curved, linear, curvilinear, angular, etc.).

The flow control assembly 200 can also include a first anchoring element 214a and a second anchoring element 214b configured to secure the flow control assembly 200 to the outflow portion (e.g., via fasteners, adhesives, bonding, etc.). The first and second anchoring elements 214a-b can be located at opposite ends of the flow control assembly 200 and can extend entirely around the outflow portion to secure the flow control assembly 200 thereto. For example, as best seen in FIGS. 2C and 2D, the first and second anchoring elements 214a-b can include respective tab structures 215a-b extending along the outflow portion and toward the gating element 202. The tab structures 215a-b can extend partially around a region of the outflow portion (e.g., a back and/or lower surface—not shown) opposite or otherwise spaced apart from the first and second actuation elements 208a-b.

The gating element 202 and first and second actuation elements 208a-b can be positioned between the first and second anchoring elements 214a-b, with the first and second actuation elements 208a-b coupled, respectively, to the first and second anchoring elements 214a-b. For example, in the illustrated embodiment (best seen in FIG. 2B), the first actuation element 208a includes a first end portion 216a coupled to the gating element 202 and a second end portion 218a coupled to the first anchoring element 214a; and the second actuation element 208b includes a first end portion 216b coupled to the gating element 202 and a second end portion 218b coupled to the second anchoring element 214b. In some embodiments, the first and second actuation elements 208a-b are fabricated separately from and subsequently coupled to the gating element 202 and/or first and second anchoring elements 214a-b (e.g., via adhesives, fasteners, bonding, etc.). In other embodiments, however, the first and second actuation elements 208a-b can be formed integrally as a single unitary component with the gating element 202 and/or first and second anchoring elements 214a-b.

In some embodiments, the first and second actuation elements 208a-b include one or more shape memory materials configured to at least partially transition from a first phase/state (e.g., a martensitic or intermediate state) to a second phase/state (e.g., an intermediate or austenitic state) upon application of energy, as previously described. The first and second actuation elements 208a-b can each be configured to change in shape or otherwise transform between a first configuration (e.g., a shape different from a memory shape) and a second configuration (e.g., the memory shape) via a shape memory effect (e.g., when heated). For example, in some embodiments, the memory shape is a lengthened configuration, while in other embodiments the memory shape is a shortened configuration. In some embodiments, the first and second actuation elements 208a-b can each be transformed into a lengthened configuration by moving the apices 210 and/or struts 212 further away from each other (e.g., along a longitudinal direction). Conversely, the first and second actuation elements 208a-b can each be transformed into a shortened configuration by moving the apices 210 and/or struts 212 closer to each other (e.g., along a longitudinal direction). In the contracted configuration, the struts 212 can be generally parallel to each other.

For example, the first actuation element 208a can be configured to transform to a lengthened configuration in response to application of energy (e.g., heating) to move the gating element 202 in a first direction (e.g., $D_2$) and the second actuation element 208b can be configured to transform to a lengthened configuration in response to application of energy to move the gating element 202 in a second, opposite direction (e.g., $D_1$). In other embodiments, the first actuation element 208a can be configured to transform to a shortened configuration in response to application of energy to move the gating element 202 in a first direction (e.g., $D_1$), and the second actuation element 208b can be configured to transform to a shortened configuration in response to application of energy to move the gating element 202 in a second, opposite direction (e.g., $D_2$).

In some embodiments, the anchoring elements 214a-b are affixed to the outflow portion of the drainage element such that the positions of the first and second anchoring elements 214a-b are stationary relative to the outflow portion and the overall length of the flow control assembly (e.g., as measured between the first and second anchoring elements 214a-b) remains constant or generally constant. As a result, the first and second actuation elements 208a-b can be configured to oppose each other, such that a change in shape of one actuation element produces a corresponding deflection and/or deformation of the other actuation element, even if energy is not applied to the other actuation element. For example, as shown in the illustrated embodiment, transformation of the second actuation element 208b into a lengthened configuration can cause the first actuation element 208a to transform into a shortened configuration, and/or transformation of the first actuation element 208a into a shortened configuration can cause the second actuation element 208b to transform into a lengthened configuration.

In some embodiments, the first and second actuation elements 208a-b are each individually actuated by applying energy to the entire actuation element. In other embodiments the energy can be applied to only a portion of the actuation element. For example, energy can be applied to a plurality of different locations, such as to one or more apices 210 and/or to one or more struts 212 of the selected actuation element(s). In such embodiments, the energy can be applied to each of the different locations simultaneously or can be applied to different locations at different times (e.g., sequentially). As a result, the extent of the shape change can be modulated based on the number of locations at which the stimulus is applied. For example, applying energy to a greater number of locations can produce a larger shape change, while applying energy to a fewer number of locations can produce a smaller shape change.

In other embodiments, rather than having the first and second actuation elements 208a-b coupled respectively to opposite sides of the gating element 202 as shown in FIGS. 2A-2D, the assembly 200 can include one or more actuation elements coupled to only a single side of the gating element 202. In such embodiments the position of the gating element 202 can be adjusted by applying energy to the actuation element(s) at the single side of the gating element 202.

FIGS. 3A-3D are side cross-sectional views of actuation elements with various low-profile shapes configured in accordance with further embodiments of the present technology. Any of the features of the embodiments of FIGS. 3A-3D can be combined with each other or incorporated in the actuation elements 208a-b of FIGS. 2A-2D. Likewise, the actuation elements of FIGS. 3A-3D can include any of the features of actuation elements 208a-b, and can be implemented as part of an intraocular shunting system (e.g., system 200 of FIGS. 2A-2D) as described herein.

Figure 3A:
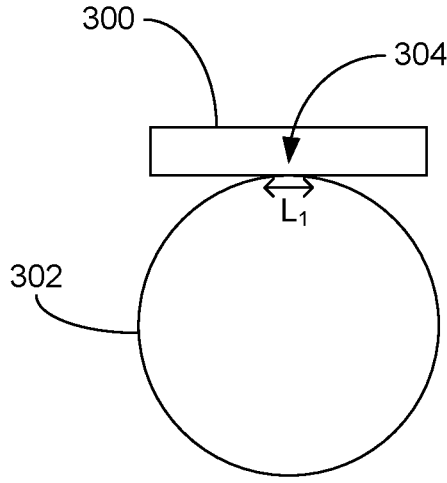
FIGS. 3A-3D are side cross-sectional views of actuation elements with various low-profile shapes configured in accordance with further embodiments of the present technology.

FIG. 3A, for example, illustrates a flattened or planar actuation element 300 coupled to an outflow portion 302 of a drainage element (not shown). The flattened actuation element 300 can be positioned adjacent or near the outflow portion 302 so that the actuation element 300 has an interface region 304 that contacts, engages, or is otherwise in close proximity with the outflow portion 302. The interface region 304 can have a cross-sectional length $L_1$ that is less than the perimeter (e.g., circumference) of the outflow portion 302. For example, length $L_1$ can be no more than 5%, 10%, 15%, or 20% of the perimeter of the outflow portion 302. In some embodiments, length $L_1$ extends no more than 5 degrees, 10 degrees, 15 degrees, 20 degrees, 25 degrees, or 30 degrees around the circumference of the outflow portion 302.

Figure 3B:
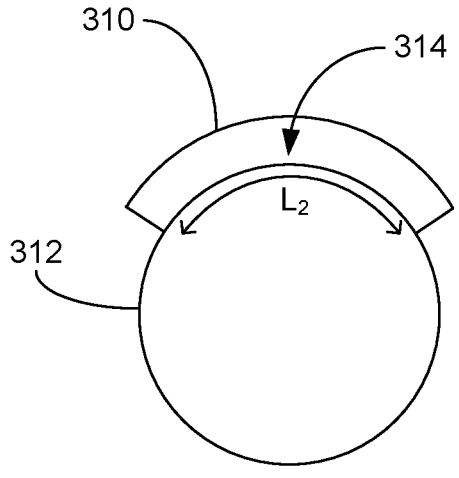

FIG. 3B illustrates a curved or arcuate actuation element 310 coupled to an outflow portion 312. The curved actuation element 310 can extend partially around the outflow portion 312 (e.g., less than halfway around the outflow portion 312). In some embodiments, the curvature of the curved actuation element 310 is similar to the curvature of the outflow portion 312 so that the curved actuation element 310 generally conforms to the surface of the outflow portion 312. The curved actuation element 310 can be positioned adjacent or near the outflow portion 312 so that the actuation element 310 has an interface region 314 (e.g., a curved surface) that contacts, engages, or is otherwise in close proximity with the outflow portion 312. The interface region 314 can have a cross-sectional length and/or arc length $L_2$ that is less than the perimeter (e.g., circumference) of the outflow portion 312. For example, length $L_2$ can be no more than 5%, 10%, 15%, 20%, 25%, 30%, 35%, 40%, 45%, or 50% of the perimeter of the outflow portion 302. In some embodiments, length $L_2$ extends no more than 30 degrees, 40 degrees, 45 degrees, 50 degrees, 60 degrees, 70 degrees, 80 degrees, or 90 degrees around the circumference of the outflow portion 312.

Figure 3C:
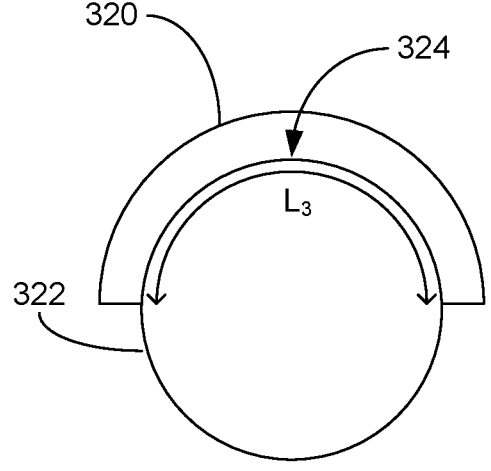

FIG. 3C illustrates a curved or arcuate actuation element 320 coupled to an outflow portion 322 and configured in accordance with another embodiment of the present technology. The curved actuation element 320 can be identical or generally similar to the curved actuation element 310 of FIG. 3B, except that curved actuation element 320 has a semicircular cross-sectional shape and extends halfway around the outflow portion 322. Accordingly, the interface region 324 of the curved actuation element 320 can have a cross-sectional length and/or arc length $L_3$ that is about 50% of the perimeter (e.g., circumference) of the outflow portion 322. In some embodiments, length $L_3$ extends no more than 90 degrees, 110 degrees, 120 degrees, 130 degrees, 135 degrees, 140 degrees, 150 degrees, 160 degrees, 170 degrees, or 180 degrees around the circumference of the outflow portion 322.

Figure 3D:
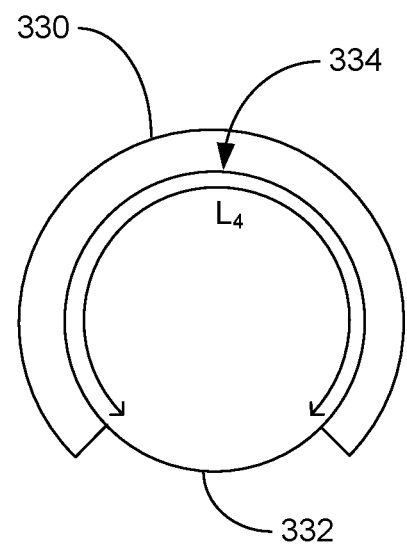

FIG. 3D illustrates a curved or arcuate actuation element 330 coupled to an outflow portion 332 and configured in accordance with a further embodiment of the present technology. The curved actuation element 330 can be identical or generally similar to the curved actuation element 310 of FIG. 3B and the curved actuation element 320 of FIG. 3C, except that curved actuation element 330 extends mostly but not entirely around the outflow portion 332 (e.g., more than halfway around the outflow portion 332). Accordingly, the interface region 334 of the curved actuation element 320 can have a cross-sectional length and/or arc length $L_4$ that is no more than about 55%, 60%, 65%, 70%, 75%, 80%, 85%, 90%, or 95% of the perimeter (e.g., circumference) of the outflow portion 332. In some embodiments, length $L_4$ extends no more than 180 degrees, 190 degrees, 200 degrees, 210 degrees, 220 degrees, 225 degrees, 230 degrees, 240 degrees, 250 degrees, 260 degrees, 270 degrees, 280 degrees, 290 degrees, 300 degrees, 310 degrees, 315 degrees, 320 degrees, 330 degrees, 340 degrees, or 350 degrees around the circumference of the outflow portion 332.

Although the outflow portions of FIGS. 3A-3D are illustrated as having circular cross-sectional shapes, in other embodiments the outflow portions can have different cross-sectional shapes (e.g., a semicircular, elliptical, semielliptical, square, rectangular, polygonal, curvilinear, rectilinear, or other shape). In such embodiments the shapes of the actuation elements of FIGS. 3A-3D can be modified accordingly to conform to, contact, engage, or otherwise interface with the outflow portions.

As one of skill in the art will appreciate from the disclosure herein, various components of the intraocular shunting systems described above can be omitted without deviating from the scope of the present technology. Likewise, additional components not explicitly described above may be added to the intraocular shunting systems without deviating from the scope of the present technology. Accordingly, the systems described herein are not limited to those configurations expressly identified, but rather encompasses variations and alterations of the described systems.

EXAMPLES

Several aspects of the present technology are set forth in the following examples:

1. An adjustable shunting system, comprising:
    a drainage element configured for placement in a patient; and
    a flow control assembly comprising
        a gating element operably coupled to the drainage element,
        a first actuation element coupled to the gating element, and
        a second actuation element coupled to the gating element,
        wherein the first and second actuation elements each extend less than entirely around a perimeter of the drainage element, and
        wherein, in response to receiving energy, the first and second actuation elements are configured to selectively move the gating element between at least a first position and a second position to change a flow resistance through the drainage element.

2. The system of example 1 wherein at least one of the first and second actuation elements extends less than 180 degrees around the perimeter.

3. The system of example 1 wherein at least one of the first and second actuation elements extends less than 90 degrees around the perimeter.

4. The system of example 1 wherein the first and second actuation elements each interface with the drainage element over a region having an arc length less than the perimeter.

5. The system of any one of examples 1-4 wherein at least one of the first and second actuation elements has a flattened or planar shape.

6. The system of any one of examples 1-4 wherein at least one of the first and second actuation elements has a curved or arcuate shape.

7. The system of any one of examples 1-6 wherein the drainage element includes one or more apertures permitting fluid flow therethrough, and wherein the gating element is movable between the first position covering the one or more apertures and the second position in which the one or more apertures are accessible.

8. A system for draining fluid from a first body region to a second body region of a patient, the system comprising:
    a drainage element having an inflow portion configured for placement within the first body region and an outflow portion configured for draining to the second body region of the patient; and
    a flow control assembly comprising—
        a gating element operably coupled to the outflow portion,
        a first actuation element coupled to the gating element, and
        a second actuation element coupled to the gating element,
        wherein the first and second actuation elements each extend about only a portion of the perimeter of the outflow portion,
        wherein the first and second actuation elements are configured to move the gating element to a selected orientation relative to the outflow portion, and
        wherein a fluid resistance through the outflow portion varies based on the selected orientation of the gating element.

9. The system of example 8 wherein the gating element extends entirely around the outflow portion.

10. The system of example 8 or example 9 wherein the first and second actuation elements each include an interface region adjacent or near the perimeter of the outflow portion, the interface region having a cross-sectional length less than the perimeter of the outflow portion.

11. The system of any one of examples 8-10 wherein the gating element includes an opening formed therein, and wherein:
    when the gating element is in the first position, the opening is spaced apart from the one or more apertures, and
    when the gating element is in the second position, the opening is near or adjacent to the one or more apertures.

12. The system of any one of examples 8-11 wherein at least one of the first and second actuation elements extends less than 180 degrees around the perimeter.

13. The system of any one of examples 8-11 wherein at least one of the first and second actuation elements extends less than 90 degrees around the perimeter.

14. The system of any one of examples 8-13 wherein the first actuation element is actuatable to move the gating element in a first direction and the second actuation element is actuatable to move the gating element in a second direction opposite the first direction.

15. The system of any one of examples 8-14 wherein the first actuation element and the second actuation element are composed of a shape memory material.

16. The system of any one of examples 8-14 wherein the first and second actuation elements are each configured to transform between a shortened configuration and a lengthened configuration via a shape memory effect.

17. The system of any one of examples 8-16 wherein the first and second actuation elements each interface with the outflow portion over a region having an arc length less than the perimeter.

18. The system of any one of examples 8-17 wherein at least one of the first and second actuation elements has a flattened or planar shape.

19. The system of any one of examples 8-17 wherein at least one of the first and second actuation elements has a curved or arcuate shape.

20. The system of any one of examples 8-17 wherein at least one of the first and second actuation elements includes one or more apices coupled to one or more struts.

21. The system of any one of examples 8-20 wherein the outflow portion includes one or more apertures permitting fluid flow therethrough, and wherein the gating element is movable between a first position covering the one or more apertures and a second position in which the one or more apertures are accessible.

22. The system of any one of examples 8-21 wherein the flow control assembly further comprises a first anchoring element coupled to the first actuation element and a second anchoring element coupled to the second actuation element, and wherein the gating element and the first and second actuation elements are positioned between the first and second anchoring elements.

23. The system of any one of examples 8-22 wherein the first actuation element is coupled to a first side of the gating element and the second actuation element is coupled to a second side of the gating element opposite the first side.

24. A method for selectively controlling fluid flow from a drainage element in an eye of a patient, the method comprising:

adjusting a position of a gating element carried by the drainage element to selectively control an amount of fluid flow through the drainage element, wherein adjusting the position of the gating element comprises applying energy, from a source external to the patient, to an actuation element coupled to the gating element, and wherein the actuation element extends only partially around the drainage element.

25. The method of example 24 wherein the actuation element is a first actuation element, and wherein the method further comprises adjusting the gating element to a different position by applying energy, from the source external to the patient, to a second actuation element coupled to the gating element, and wherein the second actuation element has a low-profile shape extending partially around the drainage element.

26. The method of example 24 or example 25 wherein the first actuation element is configured to move the gating element in a first direction in response to application of energy and the second actuation element is configured to move the gating element in a second direction opposite the first direction in response to application of energy.

27. The method of example 24 wherein the actuation element is coupled to a single side of the gating element, and wherein the position of the gating element is adjusted by applying energy only to the actuation element at the single side of the gating element.

28. The method of any one of examples 24-27 wherein the energy is applied via a laser or inductive coupling.

29. The method of any one of examples 24-28 wherein the energy causes heating of the actuation element.

30. The method of any one of examples 24-29 wherein the heating changes a shape of the actuation element via a shape memory effect.

31. The method of example 30 wherein the change in shape comprises a change in length.

32. The method of any one of examples 24-31 wherein the drainage element comprises an inflow portion positioned within an anterior chamber of the eye and an outflow portion at a different location of the eye, and wherein the gating element is operably coupled to the outflow portion.

33. The method of any one of examples 24-32 wherein the applied energy does not cause damage to surrounding cells.

34. A method of shunting fluid using an adjustable flow shunt implanted in a patient and having an actuation element that extends only partially around the shunt, the method comprising:

applying energy, from a source external to the patient, to the actuation element; and inducing, via the applied energy, a geometry change in the actuation element to change the flow resistance through the adjustable flow shunt.

An intraocular shunting system, comprising:

a drainage element configured for placement in an eye of a patient; and a flow control assembly comprising— a gating element operably coupled to the drainage element, a first actuation element coupled to the gating element, and a second actuation element coupled to the gating element, wherein the first and second actuation elements each extend less than entirely around a perimeter of the drainage element, and wherein, in response to receiving energy, the first and second actuation elements are configured to selectively move the gating element between at least a first position and a second position to change a flow resistance through the drainage element.

36. A shunting system for selectively controlling fluid flow from an anterior chamber of an eye of a patient, the system comprising:

a drainage element having an inflow portion configured for placement within the anterior chamber outside of an optical field of view of the patient and an outflow portion configured for draining to a drainage system of the eye; and a flow control assembly comprising— a gating element operably coupled to the outflow portion, a first actuation element coupled to the gating element, and a second actuation element coupled to the gating element, wherein the first and second actuation elements each extend about only a portion of the perimeter of the outflow portion, wherein the first and second actuation elements are configured to move the gating element to a selected orientation relative to the outflow portion, and wherein a fluid resistance through the outflow portion varies based on the selected orientation of the gating element.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the intraocular shunts described herein may be combined with any of the features of the other intraocular shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with intraocular shunts have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An implantable, adjustable shunting system for treating a patient, the system comprising:

a drainage element configured to shunt fluid between a first body region and a second body region of the patient;

an aperture in fluid communication with the drainage element; and an actuation assembly configured to control a fluid resistance through the aperture to at least partially control a flow of fluid through the drainage element, the actuation assembly including— a gating element, a first planar actuation element coupled to the gating element, wherein, when actuated, the first planar actuation element is configured to move the gating element relative to the aperture in a first direction to decrease fluid resistance through the aperture, and a second planar actuation element coupled to the gating element, wherein, when actuated, the second planar actuation element is configured to move the gating element relative to the aperture in a second direction to increase fluid resistance through the aperture.

2. The system of claim 1 wherein the first planar actuation element and the second planar actuation element extend in the same plane.

3. The system of claim 1 wherein the drainage element has a central axis extending therethrough, and wherein the first planar actuation element and the second planar actuation element extend in a plane parallel or at least about parallel to the central axis of the drainage element.

4. The system of claim 3 wherein, when actuated, the first planar actuation element and the second planar actuation element are configured to translate within the plane that is parallel or at least about parallel to the central axis of the drainage element.

5. The system of claim 3 wherein the first planar actuation element has a first longitudinal axis and the second planar actuation element has a second longitudinal axis, and wherein the first longitudinal axis and the second longitudinal axis are parallel or at least about parallel to the central axis of the drainage element when the adjustable shunting system is implanted in a patient.

6. The system of claim 1 wherein the first planar actuation element and the second planar actuation element each have a serpentine shape.

7. The system of claim 1 wherein the first planar actuation element and the second planar actuation element are composed of a shape memory material.

8. The system of claim 1 wherein the first direction is opposite the second direction.

9. The system of claim 1 wherein the drainage element is a tubular element.

10. An implantable, adjustable shunting system for treating a patient, the system comprising:

a drainage element configured to shunt fluid between a first body region and a second body region of the patient, the drainage element having a central axis extending therethrough;

an aperture in fluid communication with the drainage element; and a flat actuation assembly configured to control a fluid resistance through the aperture to at least partially control a flow of fluid through the drainage element, wherein the flat actuation assembly extends within a plane that is parallel or at least about parallel to the central axis of the drainage element.

11. The system of claim 10 wherein the flat actuation assembly includes an actuation element, and wherein the actuation element has a longitudinal axis that is parallel or at least about parallel to the central axis when the adjustable shunting system is implanted in the patient.

12. The system of claim 11 wherein, when actuated, the actuation element is configured to translate within the plane that is parallel to or at least about parallel to the central axis.

13. The system of claim 11 wherein the actuation element is composed of a shape memory material.

14. The system of claim 11 wherein the actuation element has a serpentine shape.

15. The system of claim 10 wherein the drainage element is a tubular element.

16. A method adjusting fluid flow through an adjustable shunt implanted in a patient and having an actuation element coupled to a drainage element, the method comprising:

applying energy, from a source external to the patient, to the actuation element to move the actuation element relative to the drainage element, wherein the actuation element extends within a plane that is a parallel to a central axis of the drainage element, and wherein moving the actuation element relative to the drainage element changes a fluid resistance through the adjustable shunt.

17. The method of claim 16 wherein the actuation element has a longitudinal axis that is parallel to or at least about parallel to the central axis.

18. The method of claim 16 wherein the actuation element is a first actuation element and moving the first actuation element relative to the drainage element decreases the fluid resistance through the adjustable shunt, and wherein the method further comprises applying energy to a second actuation element of the adjustable shunt to move the second actuation element relative to the drainage element to increase the fluid resistance through the adjustable shunt.

19. The method of claim 16 wherein applying energy, from the source external to the patient, includes using a laser to direct laser energy at the actuation element.

20. The method of claim 19 wherein the laser energy heats the actuation element, and wherein heating the actuation element causes the actuation element to move relative to the drainage element.

21. The method of claim 20 wherein the actuation element is composed of a shape memory material.

22. The method of claim 16 wherein the drainage element is a tubular element.

* * * * *